United States Patent [19]
Suzuki et al.

[11] Patent Number: 5,112,754
[45] Date of Patent: May 12, 1992

[54] TISSUE PLASMINOGEN-ACTIVATING FACTOR AND NONOCLONAL ANTIBODY

[75] Inventors: Akira Suzuki, Utsunomiya; Yasuharu Itagaki, Ohazaishibashi; Kanji Higashio, Kawagoe, all of Japan

[73] Assignee: Snow Brand Milk Products Co., Ltd., Sapporo, Japan

[21] Appl. No.: 483,800

[22] Filed: Feb. 23, 1990

Related U.S. Application Data

[63] Continuation of Ser. No. 841,818, Mar. 20, 1986, abandoned.

[30] Foreign Application Priority Data

Mar. 26, 1985 [JP] Japan .................................. 60-61716

[51] Int. Cl.⁵ ........................ A61K 37/547; C12N 9/48
[52] U.S. Cl. ................................. 435/212; 424/94.64; 435/219; 436/548; 530/413; 530/388.25; 530/388.26; 935/104; 935/108
[58] Field of Search ............................... 530/387, 413; 435/70.21, 240.27, 172.2, 948, 70.3, 212, 219; 436/548; 935/104, 108, 110; 424/94.64

[56] References Cited

U.S. PATENT DOCUMENTS 4,568,544 2/1986 Hasegawa et al. .................... 424/94
4,889,808 12/1989 Rappaport ........................ 435/69.4

*Primary Examiner*—Jeffrey E. Russel
*Attorney, Agent, or Firm*—Oblon, Spivak, McClelland, Maier & Neustadt

[57] ABSTRACT

A novel tissue plasminogen activator having the following characteristics: molecualr weight of 65,000–72,000 Daltons as measured by SDS-PAGE electrophoresis using at 7.5% agarose gel; plasminogen activator specific activity of about $10.4 \times 10^4$ IU/mg, wherein specific activity is defined as the ratio of fibrinolytic activity of purified t-PA measured on fibrin-agarose plates to milligrams of protein; about 83.1% absorption of t-PA by a fibrin-Sepharose column when applied; binds to a Concanavalin A column when applied; the fibrinolytic activity is substantially undiminished by heating at 60° C. for 60 minutes or 95° C. for 5 minutes relative to unheated t-PA; unreactive with polyclonal antisera raised against urokinase; the fibrinolytic activity is substantially stable at pH 5–10; exhibits fibrinolytic activity at pH 7.5–9.0 and temperature 39°–41° C.; a Km value of about $1.16 \times 10^{-3}$ mol/liter and a $V_{max}$ of about $11.7 \times 10^{-8}$ mol/liter for substrate S-2288; and fibrinolytic activity is inhibited by $Co^{2+}$, $Zn^{2+}$, $Cd^{2+}$, $Hg^{2+}$, $Ni^{2+}$ and $Cu^{2+}$.

3 Claims, 2 Drawing Sheets

AMOUNT CHARGED : 530,000 IU
FRACTION VOLUME : 2.5ml/TUBE
ELUTING SOLUTION: 0.1M GLYCINE-HCl BUFFER SOLUTION (pH 2.5) + 0.5M NaCl

AMOUNT CHARGED : 530,000 IU
FRACTION VOLUME : 2.5ml/TUBE
ELUTING SOLUTION: 0.1M GLYCINE-HCl BUFFER
                  SOLUTION (pH 2.5) + 0.5M NaCl

TISSUE PLASMINOGEN-ACTIVATING FACTOR AND NONOCLONAL ANTIBODY

This is a continuation of application Ser. No. 06/841,818, filed on Mar. 20, 1986, now abandoned.

BACKGROUND OF THE INVENTION

1. Field of the Invention

This invention relates to a monoclonal antibody against a plasminogen-activating factor produced by the culture of fibroblasts derived from human fetal lung tissue. More particularly, it relates to a monoclonal antibody against the non-urokinase type plasminogen-activating factor obtained by culturing the aforesaid fibroblasts to cause the concurrent production of a urokinase type plasminogen-activating factor and a plasminogen-activating factor having properties different from those of the urokinase type plasminogen-activating factor, and then removing the urokinase type plasminogen-activating factor selectively from the culture medium containing both plasminogen-activating factors.

2. Description of the Prior Art

In the treatment of thromboembolic disorders, urokinase isolated from human urine or a culture of kidney cell, and streptokinase isolated from the filtrate of a culture of β-hemolytic streptococci are now being used as plasminogen activators for the lysis of fibrin.

However, urokinase has a low affinity for fibrin and produces side effects such as hemorrhage due to high-dose administration. On the other hand, streptokinase is an enzyme protein derived from a microorganism and, when administered to human beings, has the possibility of causing allergy. Accordingly, it cannot be positively said that no problem is encountered in using these plasminogen activators for the treatment of thromboembolic disorders.

In recent years, attention has been focused on tissue type plasminogen activators which, unlike the aforesaid plasminogen activators, are found in tissues of the living organisms.

One such tissue type plasminogen activator was isolated from the cell-free culture medium of human melanoma cells and purified by Rijken and Collen [J.B.C., 256, 7035-7041(1981); Thromb. Haemostas. (Stuttgart), 48, 294-296(1982)], and it was distinguished by its molecular weight from the aforesaid urokinase and streptokinase. Thereafter, as regards this tissue type plasminogen activator derived from human melanoma cells, Pennica et al. [Nature, 301, 214-221(1983)] determined its amino acid sequence defining the primary structure of its molecule, and Bennet [Thromb. Haemostas., 50, 106(1983)] demonstrated that there are two variants having the sugar chain attached to different positions, and that their molecular weights differ from each other by 3000.

As other tissue type plasminogen activators, Vetterlain et al. [J.B.C., 254, 575-578(1979); J.B.C., 255, 3665-3672(1980)] have reported the plasminogen activators produced by normal fibroblast strain IMR-90 derived from human fetal lung tissue, and have shown that these plasminogen activators include a urokinase type plasminogen activator having a molecular weight of 50,000 to 60,000 and a new type of plasminogen activator having a molecular weight of 73,000 and incapable of being neutralized with anti-urokinase antibodies.

Moreover, Wilson et al. [Cancer Research, 40, 933-938(1980)] have also confirmed that fibroblasts derived from the lung tissue of an 8-weeks-old human fetus produce a urokinase type plasminogen activator having a molecular weight of 60,000 and a new type of plasminogen activator having a molecular weight of about 70,000 and incapable of being neutralized with anti-urokinase antibodies.

On the other hand, there has recently been published an invention relating to the preparation of a monoclonal antibody of the aforesaid tissue type plasminogen activator derived from human melanoma cells (Japanese Patent Laid-Open No. 5121/'84). In this invention, mouse myeloma cells were fused with spleen cells from a mouse immunized with the tissue type plasminogen activator derived from human melanoma cells. Thus, there were obtained 40 hybridomas capable of producing an antibody to the aforesaid plasminogen activator. It is shown, however, that the antibodies produced by only 5 hybridomas were specific for the aforesaid plasminogen activator and the antibodies produced by most of the other hybridomas exhibited a cross reaction with both the aforesaid plasminogen activator and urokinase. According to the teachings of the invention, this is not attributable to the fact that the aforesaid tissue type plasminogen activator used as the antigen was contaminated with urokinase, but to the fact that the aforesaid plasminogen and urokinase are cross reacting materials, i.e., these two enzymes have common antigenic determinants.

The method for isolating and purifying the aforesaid new type of plasminogen activator produced by normal fibroblasts derived from human fetal lung tissue has not yet been established. Consequently, its immunochemical properties and primary structure have not been elucidated.

Accordingly, it is not yet clear whether or not the aforesaid plasminogen activator produced by normal fibroblasts derived from human fetal lung tissue is the same substance as the aforesaid tissue type plasminogen activator derived from human melanoma cells, and whether or not their molecules have different primary structures.

In this connection, there has recently been proposed a method for isolating the aforesaid new type of plasminogen activator derived from human normal fibroblasts by using a zinc chelate column, fibrin column, concanavalin A-Sepharose column, arginine-Sepharose column or the like (Japanese Patent Laid-Open No. 51220/'84).

In this method, however, such columns fail to bind the aforesaid plasminogen activator specifically, so that it is impossible to obtain the plasminogen activator in a highly pure form and in a high recovery. Thus, this method lacks practical utility.

Moreover, a purification method using a specific antibody obtained from an antiserum against the aforesaid plasminogen activator is also conceivable. However, since such an antibody is a mixture, this method has the disadvantage that the titer of the antibody per unit weight of protein is low, its affinity for the plasminogen activator and its stability are not uniform, and the column chromatography cannot be carried out under consistent conditions. For these reasons, the efficiency of the adsorption to the column is low and the recovery of the plasminogen activator is not satisfactorily high.

SUMMARY OF THE INVENTION

It is an object of the present invention to provide a novel monoclonal antibody specific for a new type of plasminogen activator produced by the culture of fibroblasts derived from human fetal lung tissue.

It is another object of the present invention to provide a method for preparing the aforesaid monoclonal antibody.

It is still another object of the present invention to provide a method for purifying the aforesaid plasminogen activator to a satisfactorily high purity with the aid of the aforesaid monoclonal antibody, and a method for detecting the aforesaid plasminogen activator.

Other objects and features of the present invention will become apparent from the following detailed description.

DETAILED DESCRIPTION OF THE INVENTION

Figure 1:
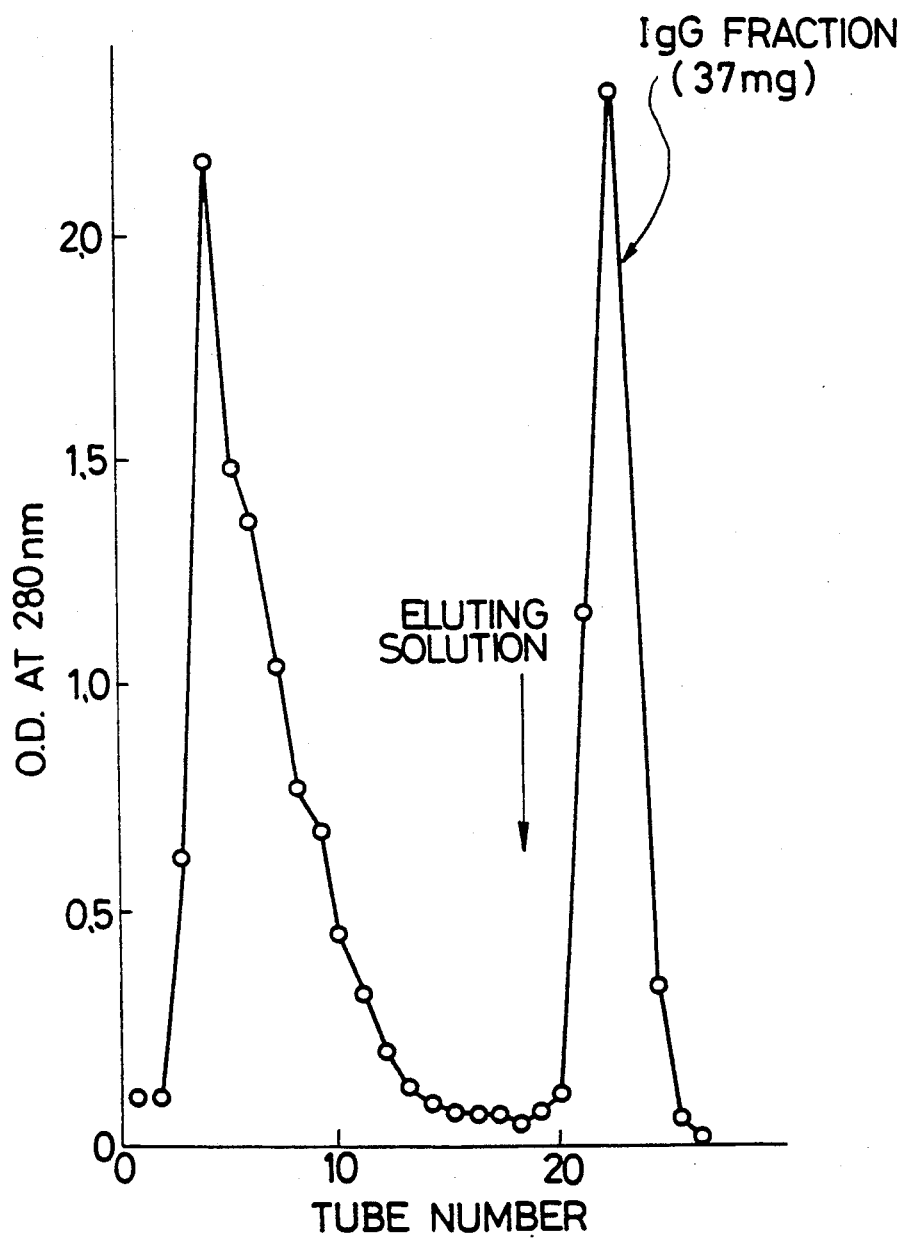
FIG. 1 illustrates the results of the purification of a monoclonal antibody against a plasminogen activator as described in Example 1.

In accordance with several features of the present invention, there are provided (1) a monoclonal antibody specific for a plasminogen activator produced by fibroblasts derived from human fetal lung tissue, characterized by having a molecular weight of about 150,000, belonging to the IgG1 or IgG2b subclass, and having an isoelectric point of 5.10 to 6.25; (2) a method for the preparation of a monoclonal antibody specific for a plasminogen activator produced by fibroblasts derived from human fetal lung tissue which comprises the steps of fusing mouse myeloma cells with spleen cells from a mouse immunized with the plasminogen activator, culturing cells of the resulting hybridomas to produce a monoclonal antibody against the plasminogen activator, and recovering the monoclonal antibody; (3) a method for the purification of a plasminogen activator produced by fibroblasts derived from human fetal lung tissue which comprises the steps of providing a chromatographic column containing the aforesaid monoclonal antibody, passing a fluid containing the plasminogen activator through the column to cause the plasminogen activator to become adsorbed thereto, and eluting the adsorbed plasminogen activator; and (4) a method for the detection of a plasminogen activator present in various tissues and various culture media which comprises the step of carrying out an enzyme-immunoassay using the aforesaid monoclonal antibody.

The plasminogen activator to which the present invention is directed exhibits immunochemical reactions different from those of the above-described tissue type plasminogen activator originating from human melanoma. This is based on the following findings.

A total of 130 hybridomas were obtained by fusing mouse myeloma cells with spleen cells from a mouse immunized with a plasminogen activator produced by fibroblasts derived from human fetal lung tissue. When the antibodies produced by these hybridomas were examined for specificity, it was confirmed that all of the antibodies were specific only for the aforesaid plasminogen activator and exhibited no cross reaction with urokinase. This has revealed that there is no common antigenic determinant between these plasminogen activators.

Accordingly, it can be said that the term "plasminogen activator" as used herein means the new type of plasminogen activator obtained by removing the urokinase type plasminogen activator from the plasminogen activators produced by fibroblasts derived from human fetal lung tissue.

According to the present invention, a monoclonal antibody specific for the new type of plasminogen activator produced by fibroblasts derived from human fetal lung tissue is characterized by the following properties.

(a) Molecular weight: About 150,000 (as measured by SDS-polyacrylamide electrophoresis).

(b) Immunoglobulin class Belongs to the IgG1 or IgG2 subclass (c) Isoelectric point: 5.10–6.25.

The specificity of this monoclonal antibody for the aforesaid plasminogen activator can be confirmed by the fact that, as will be described later, the aforesaid plasminogen activator alone is adsorbed when a fluid containing plasminogen activators is passed through a column of an insoluble carrier having the antibody chemically bound thereto.

The present tissue plasminogen activator has the following characteristics: molecular weight of 65,000–72,000 Daltons as measured by SDS-PAGE electrophoresis using a 7.5% agarose gel; plasminogen activator specific activity of about $10.4 \times 10^4$ IU/mg, wherein specific activity is defined as the ratio of fibrinolytic activity of purified t-PA measured on fibrin-agarose plates to milligrams of protein; about 83.1% absorption of t-PA by a fibrin-Sepharose column when applied; binds to a Concanavalin A column when applied; the fibrinolytic activity is substantially undiminished by heating at 60° C. for 60 minutes or 95° C. for 5 minutes relative to unheated t-PA; unreactive with polyclonal antisera raised against urokinase; the fibrinolytic activity is substantially stable at pH 5–10; exhibits fibrinolytic activity at pH 7.5–9.0 and temperature 39° C.–41° C.; a Km value of about $1.16 \times 10^{-3}$ mol/liter and a $V_{max}$ of about $1.7 \times 10^{-8}$ mol/liter for substrate S-2288; and fibrinolytic activity is inhibited by $Co^{2+}$, $Zn^{2+}$, $Cd^{2+}$, $Hg^{2+}$, $Ni^{2+}$ and $Cu^{2+}$.

The monoclonal antibody of the present invention can be prepared in the manner described hereinbelow.

PREPARATION OF THE MONOCLONAL ANTIBODY

Fibroblasts derived from human fetal lung tissue are cultured to obtain a culture medium containing the new type of plasminogen activator produced thereby (and also containing the urokinase type plasminogen activator concurrently produced thereby). From this culture medium, the new type of plasminogen activator is isolated in a highly pure form having a specific activity of 104,000 units/mg of protein. Then, mouse myeloma cells are fused with spleen cells from a mouse immunized with the aforesaid highly pure plasminogen activator, and cells of the resulting hybridomas are cultured to produce the desired monoclonal antibody.

In this connection, the method for isolating a highly pure form of the aforesaid plasminogen activator from the aforesaid culture medium has been developed by the present inventors Briefly stated, the aforesaid culture medium is subjected to ion exchange chromatography, and the eluted fraction (containing both the new type of plasminogen activator and the urokinase type olasminogen activator) is subjected to affinity chromatography using p-aminobenzamidine or ε-aminocaproylbenzamidine as the ligand. Thus, the urokinase type plasminogen activator present in the aforesaid eluted fraction is selectively eluted and removed. Then, the new type of plasminogen activator is eluted and the eluted fraction is subjected to gel filtration.

In the practice of the present invention, hybridomas capable of producing the aforesaid monoclonal antibody can be formed on the basis of the principle established by Kohler and Milstein [Nature, 256, 495–497(1975)], by fusing mouse B lymphocytes with mouse myeloma cells according to any of the procedures described, for example, by R. A. Goldsberg et al. [Nature, 267, 707(1977)], Masato Sugi [Seibutsu-to-Kagaku, 20, 116–122(1982)] and Shigeaki Tanaka [Tanpakushitsu-Kakusan-Koso, 26, 965–976(1981)].

FORMATION OF HYBRIDOMAS

More specifically, using Freund's complete adjuvant, the aforesaid highly pure plasminogen activator is administered, as an antigen to 6- to 8-weeks-old BALB/c strain mice in a dose of 100 to 200 μg per mouse. Usually, the plasminogen activator is injected intraperitoneally or subcutaneously on the back. The administration schedule should be such that an additional injection is given 2 weeks after the initial injection and, thereafter several additional injections are given at intervals of 2 weeks. Three days after the final injection, the spleen is excised. B cells (B lymphocytes) from the spleen and myeloma cells from a bone marrow tumor of a mouse of the aforesaid strain (e.g., p-3NS1/1-Ag4-1, hereinafter abbreviated as NS-1) are mixed in a ratio of 1:1 to 10:1 and fused together in the presence of polyethylene glycol 1000 or 1500. Then, the cells are suspended in a medium for the culture of hybridomas to a density of $1 \times 10^6$ myeloma cells/ml and the resulting suspension is sprayed over a 96-well micro titer plate in an amount of 0.1 ml per well. On the day following the cell fusion, HAT medium adjusted so as to permit the growth of fused cells is added in an amount of 0.1 ml per well. Thereafter, half of the supernatant of the culture medium is replaced by fresh HAT medium at intervals of 1 to 3 days. After about 1 week, most of the cells other than B cell-myeloma cell hybridomas are dead and colonies of such hybridomas are formed. Next in order to determine whether the hybridomas formed in this manner produce an antibody specific for the desired plasminogen activator, their capability of producing such an antibody is examined on a micro titer plate by an enzyme-immunoassay in which the cell-free culture media and the aforesaid highly-pure plasminogen activator (having a specific activity of 104,000 units/mg of protein and being SDS-electrophoretically homogeneous) are used as antigens. Then, according to the limiting diluting method, the hybridoma colonies exhibiting antibody production in the cell-free culture medium are cloned in such a way that one hybridoma cell is present in each well. After being cultured for 1 week, they are tested for antibody production by an enzyme-immunoassay.

The above-described cloning procedure is repeated five or six times to obtain stable hybridomas not undergoing the deletion of the monoclonal antibody gene. The stable hybridomas thus obtained can produce a monoclonal antibody having a high degree of specificity for the aforesaid new type of plasminogen activator. Moreover, they can be infinitely subcultured and thereby continue to produce the monoclonal antibody In order to obtain this monoclonal antibody, a stable hybridoma as obtained by the aforesaid cloning procedure is mass-cultured in RPMl-1640 medium supplemented with 10% bovine fetal serum, and the monoclonal antibody is recovered from the resulting culture medium. Alternatively, such a hybridoma is injected, in a dose of $1 \times 10^7$ cells per mouse, into the abdominal cavity of mature BALB/c strain mice to which 0.5 ml of the immunosuppressant pristane (2,6,10,14-tetramethylpentadecane) was intraperitoneally administered 1 to 2 weeks ago, and thereby grown. Then, the monoclonal antibody is recovered from the resulting ascitic fluid.

The recovery of the monoclonal antibody from the aforesaid culture medium or ascitic fluid and the purification of the recovered monoclonal antibody can be readily carried out by means of a commercially available purification system (Biorad Co.) using a protein A-affinity gel column.

Since the monoclonal antibody obtained in the above-described manner has a high degree of specificity for the new type of plasminogen activator produced by fibroblasts derived from human fetal lung tissue, the aforesaid plasminogen activator can be purified by using a column of an insoluble carrier having the monoclonal antibody chemically bound thereto and immobilized thereby. This purification method will be described hereinbelow.

METHOD FOR PURIFYING THE PLASMINOGEN ACTIVATOR WITH THE AID OF THE MONOCLONAL ANTIBODY

When a plasminogen activator-containing culture medium obtained by the culture of normal fibroblasts derived from human fetal lung tissue or a plasminogen activator-containing culture medium obtained by the culture of plasminogen activator-producing bacteria or animal cells created by genetic engineering techniques is passed through the aforesaid column of the monoclonal antibody-immobilizing carrier, the desired plasminogen activator is selectively adsorbed to the aforesaid column. Thus, the plasminogen activator can be isolated in a highly pure form and in a high yield of 90% or greater.

More specifically, since the desired new type of plasminogen activator is a protein having a considerably higher degree of hydrophobicity than that of the urokinase type plasminogen activator concurrently produced by the aforesaid culture, its adsorbability to the aforesaid column is very high (for example, 1 ml of an insoluble carrier gel having 3 to 5 mg of the monoclonal antibody bound thereto can adsorb 150,000 to 250,000 IU of the plasminogen activator). Accordingly, a large amount of the plasminogen activator can be purified by using a column of relatively small size. Moreover, this purification method not only permits a single-stage purification which greatly simplifies the operation as compared with conventional multistage column purification methods, but also makes it possible to obtain the desired plasminogen activator in a very high recovery (90% or greater) as described above. In this connection, the recoveries attained by the conventional multistage purification methods are as low as 30% to 50%.

Furthermore, the purification method of the present invention is very advantageous from an industrial point of view because the insoluble carrier of the column may be repeatedly used simply by eluting the plasminogen activator adsorbed thereto and then washing the carrier with a suitable buffer solution in the neutral region.

The insoluble carrier used for this purpose can be any carrier that is commonly used in affinity chromatography.

Now, some enzymatic properties of the new type of purified plasminogen activator in accordance with the present invention are shown in Table 1, which also includes those of urokinase for comparative purposes.

TABLE 1

|   | New type of plasminogen activator | Urokinase |
|---|---|---|
| (1) Molecular weight (as measured by SDS-electrophoresis) | 65,000–72,000 | 55,000 (high-molecular type) 33,000 (low-molecular type) |
| (2) Specific activity (IU/mg) | $10.4 \times 10^4$ | $15 \times 10^4$ (high-molecular type) $23 \times 10^4$ (low-molecular type) |
| (3) Affinity for fibrin (binding rate, %) | 83.1 | 40.8 (high-molecular type) 12.5 (low-molecular type) |
| (4) Adsorbability to a concanavalin A column | Yes | No or slight |
| (5) Thermal resistance (residual activity, %) |   |   |
| Heated at 60° C. for 60 minutes | 100.0 | 0.8 |
| Heated at 95° C. for 5 minutes | 100.0 | 34.0 |
| (6) Neutralization of activity with a polyclonal antibody against urokinase | Not neutralized at all | Completely neutralized |
| (7) pH resistance | 5–10 | 1–10 |
| (8) Optimum pH range | 7.5–9.0 | 7.5–9.0 |
| (9) Temperature range suitable for action (°C.) | 39–41 | 39–41 |
| (10) Km value (mol/liter) and Vmax (mol/min-unit) for substrate S-2288 | Km: $1.16 \times 10^{-3}$ Vax: $1.7 \times 10^{-8}$ | Km: $5 \times 10^{-4}$ (high-molecular type) Vmax: $5 \times 10^{-10}$ (low-molecular type) |
| (11) Inhibitory metal ions | $Co^{2+}$, $Zn^{2+}$, $Cd^{2+}$, $Hg^{2+}$, $Ni^{2+}$, $Cu^{2+}$ | $Co^{2+}$, $Hg^{2+}$, $Ni^{2+}$, $Cu^{2+}$ |

As can be seen from Table 1, the plasminogen activator to which the present invention is directed has enzymatic properties different from those of conventional urokinase Substrate S-2288 (H.D.Ile-Pro-Arg-pNa.2HCl) is a synthetic substrate used for the determination of tissue plasminogen activator available from KabiVitrum Diagnostica, Sweden.

Just for information, the amino acid compositions of plasminogen activators derived from various types of cells as determined by Rijken and Collen [J. Biol. Chem., 256, 7035–7041(1981)] are shown in Table 2.

TABLE 2

| Amino acid | Plasminogen activator of the invention (IMR-90, t-PA) | Plasminogen activator derived from melanoma cells | | Plasminogen activator derived from uterus | |
|---|---|---|---|---|---|
| | | Single chain | Double chain | Single chain | Double chain |
| Aspartic acid | 9.3 | 9.8 | 10.5 | 11.2 | 10.0 |
| Threonine | 4.8 | 5.4 | 5.8 | 6.2 | 5.6 |
| Serine | 8.3 | 9.2 | 8.8 | 11.0 | 10.9 |
| Glutamic acid | 11.2 | 13.1 | 12.0 | 9.9 | 12.4 |
| Proline | 6.4 | 7.1 | 6.9 | 6.3 | 5.8 |
| Glycine | 15.7 | 10.4 | 9.4 | 10.8 | 13.0 |
| Alanine | 6.7 | 6.6 | 7.1 | 7.4 | 6.2 |
| Cystine | N.D. | N.D. | N.D. | N.D. | N.D. |
| Valine | 4.7 | 4.1 | 4.4 | 4.6 | 4.2 |
| Methionine | 0.8 | 0.9 | 1.1 | 1.0 | 1.0 |
| Isoleucine | 3.6 | 3.0 | 3.2 | 3.3 | 2.8 |
| Leucine | 7.0 | 8.1 | 8.5 | 7.7 | 7.2 |
| Tyrosine | 4.7 | 4.0 | 3.9 | 3.7 | 3.9 |
| Phenylalanine | 3.3 | 3.7 | 3.8 | 4.0 | 3.4 |
| Histidine | 4.4 | 3.3 | 3.2 | 3.1 | 3.2 |
| Lysine | 2.9 | 5.5 | 5.4 | 5.2 | 5.4 |
| Arginine | 6.3 | 5.9 | 6.1 | 4.6 | 5.2 |
| Tryptophan | N.D. | N.D. | N.D. | N.D. | N.D. |

(Note)
N.D. indicates that no determination was made.

In addition to the above-described purification of the plasminogen activator, the present invention also makes it possible to detect the plasminogen activator present in various tissues and various culture media with the aid of the aforesaid monoclonal antibody. This detection method will be described hereinbelow.

METHOD FOR DETECTING THE PLASMINOGEN ACTIVATOR with the aid of the monoclonal antibody According to the present invention, the detection of the plasminogen activator can be carried out by the enzyme-immunoassay technique using the aforesaid monoclonal antibody. Thus, very small amounts of the plasminogen activator present in various tissues and various culture media can be determined with high accuracy.

Accordingly, the present method for detecting the plasminogen activator may be effectively utilized, for example, in the screening of plasminogen activator-producing cells of human origin by the immunological determination of the plasminogen activator present in the culture media of various cells of human origin, and in the immunological determination of the plasminogen activator present in blood for purposes of clinical examination and the like.

In order to further illustrate the present invention and its effects, the following examples are given.

EXAMPLE 1

This example illustrates the preparation of monoclonal antibodies.

PREPARATION OF A HIGHLY PURE PLASMINOGEN ACTIVATOR

Normal fibroblasts of strain IMR-90 (ATCC, CCL-186) derived from human fetal lung tissue were cultured in a serum-free medium supplemented with 1% neopeptone (or proteose peptone) to induce the production of the desired plasminogen activator. The resulting culture medium was filtered, and the filtrate (100-120 units/ml) was passed through an SP column (an ion exchange resin column available from AMF Co.) at a flow rate of 3-6 liters/hr to cause all of the aforesaid plasminogen activator to become adsorbed thereto (in this step, the concurrently produced urokinase type plasminogen activator was also adsorbed to the column). After the column was washed with a 1/100 M acetate buffer solution (pH 4.5) containing 0.15 M NaCl, the adsorbed plasminogen activators were eluted with the aforesaid buffer solution containing 1.0 M NaCl to effect their concentration and partial purification simultaneously. Then, the resulting eluate was passed through a p-aminobenzamidine-CH/Sepharose 4B affinity column to cause the plasminogen activators to become adsorbed thereto, and the adsorbed urokinase type plasminogen activator alone was eluted by passing therethrough a 1/10 M acetate buffer solution (pH 4.0) and then a 1/100 M phosphate buffer solution (pH 7.4) containing 0.1 M arginine and 0.01% Tween 80. Subsequently, the desired plasminogen activator was eluted by passing therethrough a 1/100 M phosphate buffer solution (pH 7.4) containing 0.4 M arginine and 0.01% Tween 80. The resulting eluate was subjected to gel filtration through Sephacryl S-200 to obtain a highly purified form of the desired plasminogen activator (having a specific activity of 104,000 units/mg of protein) which was SDS-electrophoretically homogeneous and not contaminated with urokinase.

FORMATION OF HYBRIDOMAS

According to the technique previously described in detail, mouse myeloma cells were fused with spleen cells from a mouse immunized with the highly pure plasminogen activator obtained in the above-described manner. Thus, hybridomas capable of producing a monoclonal antibody to the plasminogen activator were formed.

Out of the 130 hybridoma so formed, 10 hybridomas giving the highest production of the antibody were chosen and each of them was cloned six times to establish 10 hybridoma clones.

COLLECTION OF THE MONOCLONAL ANTIBODY

Each of the 10 hybridoma clones obtained in the above-described manner was injected into the abdominal cavity of 10 to 15 pristine-treated BALB/c strain mice in a dose of $1 \times 10^7$ cells/mouse. These mice were kept until the abdomen became fully inflated, and the ascitic fluid was collected. The monoclonal antibody contained in the ascitic fluid was purified by means of a monoclonal antibody purification system (MAPS TM, Biorad Co.). The results of the purification are illustrated in FIG. 1. The amount of monoclonal antibody produced per mouse is shown in Table 3.

TABLE 3

| Productivity of Monoclonal Activity of Hybridoma Clones | |
|---|---|
| Hybridoma clone | Production of monoclonal antibody (mg/mouse) |
| NS-1, $D_2$, C-10 | 41.8 |
| NS-1, $D_2$, C-5 | 72.2 |
| NS-1, $E_2$, B-4 | 35.3 |
| NS-1, $E_2$, H-11 | 50.0 |
| NS-1, $G_1$, G-8 | 45.0 |
| NS-1, $B_1$, H-1 | 55.0 |
| NS-1, $C_1$, H-1 | 75.6 |
| NS-1, $G_1$, C-9 | 63.2 |
| NS-1, $B_3$, E-7 | 40.0 |
| NS-1, $H_4$, E-3 | 50.5 |

It can be seen from Table 3 that the amount of monocolonal antibody produced per mouse was considerably large, ranging from 35.3 to 75.6 mg.

EXAMPLE 2

In this example, the specificity of monoclonal antibodies for the desired plasminogen activator was evaluated and the immunoglobulin class or subclass to which the antibodies belong was determined.

SPECIFITY FOR THE NEW TYPE OF PLASMINOGEN ACTIVATOR

The hybridomas formed in Example 1 were cultured, and the resulting cell-free culture media were subjected to an enzyme-immunoassay (i.e., Avidin-Biotin ELISA) using the new type of plasminogen activator in highly pure form and purified urokinase as antigens. In this manner, the specificity of the monoclonal antibodies for each of the aforesaid plasminogen activators was evaluated. More specifically, with respect to each of the 130 hybridomas formed in Example 1, the aforesaid specificity was evaluated by examining the cross reactivity of the monoclonal antibody produced by each hybridoma with each of the aforesaid plasminogen activators. The results thus obtained are shown in Table 4.

TABLE 4

| Hybridoma No. | O.D. at 414 nm | |
|---|---|---|
| | Plasminogen activator | Urokinase |
| NS-1, A-2 | 0.247 | 0.061 |
| A-4 | 0.208 | 0.081 |
| A-5 | 0.210 | 0.058 |
| A-6 | 0.224 | 0.075 |
| A-7 | 0.239 | 0.087 |
| A-8 | 0.223 | 0.062 |
| A-9 | 0.214 | 0.059 |
| A-10 | 0.219 | 0.085 |
| A-11 | 0.213 | 0.081 |
| NS-1, B-1 | 0.244 | 0.084 |
| B-2 | 0.244 | 0.073 |
| B-3 | 0.248 | 0.081 |

TABLE 4-continued

| Hybridoma No. | O.D. at 414 nm | |
|---|---|---|
| | Plasminogen activator | Urokinase |
| B-4 | 0.201 | 0.059 |
| B-5 | 0.235 | 0.077 |
| B-10 | 0.230 | 0.079 |
| B-12 | 0.220 | 0.086 |
| NS-1, C-1 | 0.247 | 0.089 |
| C-2 | 0.240 | 0.089 |
| C-3 | 0.250 | 0.068 |
| C-6 | 0.231 | 0.070 |
| NS-1, C-B | 0.213 | 0.071 |
| C-9 | 0.231 | 0.081 |
| C-10 | 0.219 | 0.085 |
| NS-1, D-1 | 0.242 | 0.087 |
| D-2 | 0.266 | 0.072 |
| D-3 | 0.265 | 0.074 |
| D-4 | 0.204 | 0.076 |
| D-5 | 0.207 | 0.064 |
| D-10 | 0.216 | 0.086 |
| NS-1, E-1 | 0.227 | 0.070 |
| E-2 | 0.255 | 0.083 |
| E-3 | 0.236 | 0.077 |
| E-8 | 0.227 | 0.087 |
| E-10 | 0.215 | 0.081 |
| E-12 | 0.209 | 0.078 |
| NS-1, F-1 | 0.234 | 0.085 |
| F-2 | 0.222 | 0.070 |
| F-3 | 0.224 | 0.089 |
| Other 92 hybridomas | 0.248 −0.191 | 0.097 −0.053 |

(note)
In blank determinations (controls), the values of O.D. at 414 nm were 0.085–0.050.

IMMUNOGLOBULIN CLASS SUBCLASS

With respect to 10 out of the purified monoclonal antibodies obtained in Example 1, the immunoglobulin class or subclass to which each of them belongs was determined by an enzyme-immunoassay (i.e., ELISA) using anti-mouse immunoglobulin sera specific for several immunoglobulin classes and subclasses. The results thus obtained are shown in Table 5.

TABLE 5

| Cell system | IgG1 | IgG2b | IgG3 | IgM | κ |
|---|---|---|---|---|---|
| NS-1, D$_2$, C-10 | | + | | | + |
| NS-1, D$_2$, C-5 | | + | | | + |
| NS-1, E$_2$, B-4 | | + | | | + |
| NS-1, E$_2$, H-11 | | + | | | + |
| NS-1, G$_1$, G-8 | | + | | | + |
| NS-1, B$_1$, H-1 | + | | | | + |
| NS-1, C$_1$, H-1 | + | | | | + |
| NS-1, G$_1$, C-9 | | + | | | + |
| NS-1, B$_3$, E-7 | | + | | | + |
| NS-1, H$_4$, E-3 | + | | | | + |

(note)
By isotype analyses.

As can be seen from Table 4, the monoclonal antibodies in accordance with the present invention exhibit a cross reaction with the new type of plasminogen activator, but exhibit practically no cross reaction with urokinase. Thus, these antibodies are considered to be specific for the aforesaid plasminogen activator.

Moreover, as can seen from Table 5, these monoclonal antibodies belong to the IgG1 or IgG2b subclass of immunoglobulins.

EXAMPLE 3

This example illustrates the isolation of a pure form of the plasminogen activator from a cell culture medium by utilizing one of the monoclonal antibodies obtained in Example 1.

ISOLATION OF THE PLASMINOGEN ACTIVATOR FROM THE CULTURE MEDIUM OF NORMAL DIPLOID FIBROBLASTS DERIVED FROM HUMAN FETAL LUNG TISSUE

Fibroblasts of strain IMR-90 (ATCC, CCL-186) were cultured to obtain 4.5 liters of a serum-free culture medium (having an activity of 120 IU/ml after neutralization with a polyclonal antibody against urokinase). The monoclonal antibody produced by hybridoma clone NS-1, D$_2$, C-10 (see Example 1) was chemically bound to an Affigel-10 column (0.9 cm in diameter and 5 ml in volume; Biorad Co.) in an amount of 3.5 mg of antibody per milliliter of carrier, and the aforesaid serum-free culture medium was passed through this column. Any unadsorbed fraction was removed by washing the column with a 1/100 M phosphate buffer solution (pH 7.4) containing 0.1% Tween 80 and 0.5 M NaCl until the absorbance (O.D. at 280 nm) of the effluent from the column was not greater than 0.005. Then, the plasminogen activator adsorbed to the column was eluted with an aqueous solution (pH 7.4) containing 4 M MgCl$_2$ and 0.1% Tween 80. Some properties of the aforesaid serum-free culture medium used as the starting material and the eluted fraction obtained in the above-described manner are shown in Table 6.

TABLE 6

| Sample | Activity (IU/ml) | Total activity (IU) | Specific activity (IU/mg) | Recovery (%) |
|---|---|---|---|---|
| Serum-free culture medium | 120 | 540,000 | 56.7 | 100 |
| Eluted plasminogen activator fraction | 2,920 | 496,000 | 119,000 | 91 |

As can be seen from Table 6, a purified plasminogen activator having a significantly high specific activity was recovered from the serum-free culture medium in a yield of as high as 91%.

EXAMPLE 4

This example illustrates the purification of a crude plasminogen activator by utilizing one of the monoclonal antibodies obtained in Example 1.

PURIFICATION OF A CRUDE PLASMINOGEN ACTIVATOR

Normal diploid fibroblasts of strain GM-1604 derived from human fetal lung tissue were cultured to obtain 5.6 liters of a serum-free culture medium (having an activity of 120 IU/ml after neutralization with a polyclonal antibody against urokinase). This culture medium was adjusted to pH 4.5 with HCl and then passed through an SP column (an ion exchange resin column available from AMF Co.) to cause all of the aforesaid plasminogen activator to become adsorbed thereto This column was thoroughly washed with a 0.01 M acetate buffer solution (pH 4.5) containing 0.15 M NaCl, and then eluted with a 0.01 M acetate buffer solution containing 1 M NaCl to obtain a crude plasminogen activator solution having an activity of 530,000 IU after neutralization with a polyclonal antibody against urokinase.

The monoclonal antibody produced by hybridoma clone NS-1, E$_2$, H-11 (see Example 1) was chemically bound to a Treseal-activated Sepharose column (0.9 cm in diameter and 5 ml in volume; Pharmacia Co.) in an amount of 3.5 mg of antibody per milliliter of carrier, and the crude plasminogen activator solution obtained in the above-described manner was passed through this column.

Figure 2:
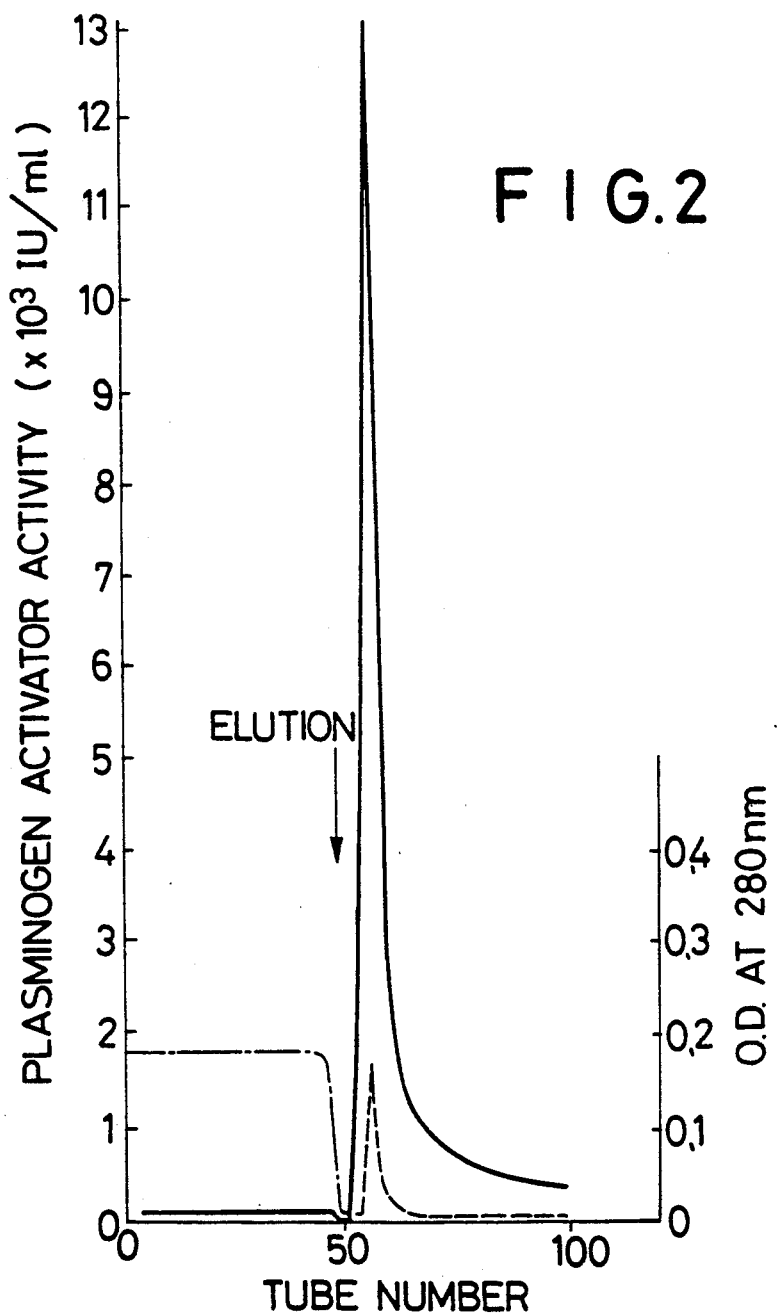
FIG. 2 illustrates the elution pattern of a purified plasminogen activator obtained by column chromatography as described in Example 4.

Any unadsorbed fraction was removed by washing the column with a 1/100 M phosphate buffer solution (pH 7.4) containing 0.1% Tween 80 and 0.5 M NaCl until the absorbance (O.D. at 280 nm) of the effluent from the column was not greater than 0.005. Then, the plasminogen activator adsorbed to the column was eluted with a glycine-HCl buffer solution (pH 2.5) containing 0.5 M NaCl and 0.1% Tween 80. Some properties of the aforesaid crude plasminogen activator solution used as the starting material and the purified plasminogen activator fraction obtained by the aforesaid elution are shown in Table 7. The elution pattern of the aforesaid purified plasminogen activator fraction is illustrated in FIG. 2.

TABLE 7

| Sample | Activity (IU/ml) | Total activity (IU) | Specific activity (IU/mg) | Recovery (%) |
|---|---|---|---|---|
| Crude plasminogen activator solution | 964 | 530,000 | 794 | 100 |
| Purified plasminogen activator fraction | 2,980 | 507,000 | 121,000 | 95.7 |

It can be seen from Table 7 that, when a crude plasminogen activator solution is purified by column chromatography using the corresponding monoclonal antibody, a purified plasminogen activator having a markedly improved specific activity is obtained in a high recovery.

EXAMPLE 5

This example illustrates an embodiment of the detection method of the present invention in which the plasminogen activators produced by various strains of normal diploid fibroblasts derived from human tissues are screened by utilizing one of the monoclonal antibodies obtained in Example 1.

Cell strains IMR-90, WI-38, MRC-5, Flow 2000, HEL-299 and GM 1604, which are normal diploid fibroblasts derived from human tissues and available from ATCC and NIH, U.S.A., were separately cultured and treated with 1% proteose peptone to induce the production of a plasminogen activator. Each of the plasminogen activators present in the resulting serum-free culture media was subjected to an enzyme-immunoassay (ELISA) using the monoclonal antibody (against the plasminogen activator produced by IMR-90) produced by hybridoma clone INS-1, D$_2$, C-10 formed in Example 1. The results thus obtained are shown in Table 8.

TABLE 8

| Normal fibroblast strain originating from human tissue | Cross reactivity |
|---|---|
| IMR-90 | + |
| IW-38 | + |
| MRC-5 | + |
| Flow-2000 | + |
| HEL-299 | + |
| GM-1604 | + |

As can be seen from Table 8, the plasminogen activators produced by the aforesaid available strains of normal fibroblasts originating from human tissues are immunochemically identical to the plasminogen activator produced by IMR-90. In other words, it has been confirmed that the plasminogen activators produced by these strains of normal fibroblasts have antigenic determinants common to the plasminogen activator produced by IMR-90.

What is claimed is:

1. A novel tissue plasminogen activator having the following characteristics: molecular weight of 65,000–72,000 Daltons as measured by SDS-PAGE electrophoresis using a 7.5% agarose gel; plasminogen activator specific activity of about $10.4 \times 10^4$ IU/mg, wherein specific activity is defined as the ratio of fibrinolytic activity of purified t-PA measured on fibrin-agarose plates to milligrams of protein; about 83.1% absorption of t-PA by a fibrin-Sepharose column when applied; binds to a Concanavalin A column when applied; the fibrinolytic activity is substantially undiminished by heating at 60° C. for 60 minutes or 95° C. for 5 minutes relative to unheated t-PA; unreactive with polyclonal antisera raised against urokinase; the fibrinolytic activity is substantially stable at pH 5–10; exhibits fibrinolytic activity at pH 7.5–9.0 and temperature 39° C.–41° C.; a Km value of about $1.16 \times 10^{-3}$ mol/liter and a $V_{max}$ of about $1.7 \times 10^{-8}$ mol/liter for substrate S-2288; and fibrinolytic activity is inhibited by $Co^{2+}$, $Zn^{2+}$, $Cd^{2+}$, $Hg^{2+}$, $Ni^{2+}$ and $Cu^{2+}$.

2. A novel tissue plasminogen activator according to claim 1, which is obtained from culture medium of normal diploid fibroblasts of strain IMR-90 (ATCC, CCL-186) derived from human fetal lung tissue.

3. A novel tissue plasminogen activator according to claim 1, obtained from culture medium of normal diploid fibroblasts derived from human fetal lung tissue, and purified by affinity chromatography using a monoclonal antibody that binds said plasminogen activator, in which a benzamidine derivative selected from the group consisting of p-aminobenzamidine and ε-aminocaproylbenzamidine is used as the ligand, said antibody having
(a) a molecular weight of about 150,000 as measured by SDS-polyacrylamide electrophoresis,
(b) an immunoglobin class belonging to the Ig G1or Ig G2b subclass, and
(c) an isolectirc point of 5.10 to 6.25.

* * * * *